(12) United States Patent
Camonis et al.

(10) Patent No.: US 6,479,237 B1
(45) Date of Patent: Nov. 12, 2002

(54) METHODS FOR DETECTING INTERACTION AMONG SEVERAL PROTEINS

(75) Inventors: Jacques Camonis, Paris (FR); Francisco Romero-Portillo, Seville (ES); Ricardo Attar, Lawrenceville, NJ (US); Jean-Marc Egly, Strasbourg (FR); Franck Tirode, Illkirch (FR)

(73) Assignees: Institut National de la Sante et de la Recherche Medicale (Inserm), Paris Cedex (FR); Centre National de la Recherche Scientifique, Paris Cedex (FR); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/402,317

(22) PCT Filed: Apr. 3, 1998

(86) PCT No.: PCT/FR98/00685
§ 371 (c)(1),
(2), (4) Date: Feb. 23, 2000

(87) PCT Pub. No.: WO98/44099
PCT Pub. Date: Oct. 8, 1998

(30) Foreign Application Priority Data

Apr. 3, 1997 (FR) .............................................. 97 04084

(51) Int. Cl.$^7$ ........................... C12Q 1/68; C12P 21/06; C12N 15/09; C12N 15/74; C07H 21/04
(52) U.S. Cl. ................... 435/6; 435/69.7; 435/320.1; 435/69.1; 435/29; 435/471; 435/476; 536/23.1; 536/23.4
(58) Field of Search ................. 435/6, 29, 69.1, 435/471, 476, 320.1, 69.7; 536/23.1, 23.4

(56) References Cited

U.S. PATENT DOCUMENTS 5,989,808 A * 11/1999 Young et al. ................... 435/6
5,994,119 A * 11/1999 Dietz ..................... 435/254.21

FOREIGN PATENT DOCUMENTS

WO    WO 95/34646    12/1995
WO    WO 96/30507    10/1996

OTHER PUBLICATIONS

J. Zhang et al., "A Yeast Three–Hybrid Method to Clone Ternary Protein Complex Components", Analytical Biochemistry, Col 242, Nov. 1996, pp. 68–72.

P. Legrain et al., "Interaction Between PRP11 and SPP91 Yeast Splicing Factors and Characterization of a PRP9–PR11–SPP91 Complex", Science vol. 262, 1993, pp. 108–110.

M.A. Osborne et al., "The Yeast Tribrid System—Genetic Detection of Trans–Phosphorylated ITAM–SH2–Interactions", Bio/Technology, vol. 13, Dec. 1995, pp. 1474–1478.

A. Hinnen et al., "Gene Expression in Recombinant Yeast", Gene Expression in Recombinant Microorganisms, Jan. 1, 1995, pp. 121–193, 146–147.

Kerjan et al., "Nucleotide Sequence of the Saccharomyces Cerevisiae MET25 Gene", Nucleic Acids Research, vol. 14, No. 20, 1986, pp. 7861–7871.

M. Johnson et al., "Sequences That Regulate the Divergent GAL1–GAL10 Promoter in Saccharomyces Cerevisiae", Molecular and Cellular Biology, vol. 4, 1984, pp. 1440–1448.

S. Fields et al., "A Novel Genetic System To Detect Protein–Protein Interactions", col. 340, Jul. 20, 1989, pp. 245–246.

F. Tirode et al., "A Conditionally Expressed Third Partner Stabilizes or Prevents the Formation of A Transcription Activator in a Three–Hybrid System", Journal of Biological Chemistry, vol. 272, No. 37, Sep. 12, 1997, pp. 22995–22999.

\* cited by examiner

Primary Examiner—David Guzo
Assistant Examiner—Gerald G. Leffers, Jr.
(74) Attorney, Agent, or Firm—Young & Thompson (57) ABSTRACT

The aim of the invention is to use at least one conditional promoter to implement a method for detecting one or more proteins interacting directly or indirectly with at least two other proteins during the formation of a protein complex, or during the inhibition of the formation of a protein complex.

8 Claims, 3 Drawing Sheets

SEQUENCE LISTING

```
<160> NUMBER OF SEQ ID NOS:  6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
agtcgtgaat tcatggctct ggacctgaag                                       30

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
gatcgtgaat tcttaaaaaa ttagtttctt gggcaa                                36

<210> SEQ ID NO 3
<211> LENGTH: 30
<212> TYPE: DNA
<213> ORGANISM: Artificial Sequence
```

-continued

```
<220> FEATURE:
<223> OTHER INFORMATION: Description of Artificial Sequence:
      Oligonucleotide

<400> SEQUENCE: 3
gatcgtgcgg ccgcaatgta ccacaacagt                                    30

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
gatcgtgcgg ccgcttagag agattctacc ag                                 32

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
gatcaggaat tcccatggag gatcagggtt                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
gatcaggaat tcttaactgg gctgccagaa                                    30
```

METHODS FOR DETECTING INTERACTION AMONG SEVERAL PROTEINS

The present invention relates to methods for detecting or identifying proteins involved in the formation of a protein complex, or in the inhibition of the formation of a protein complex.

Among the methods currently available for studying interactions between proteins, the two-hybrid system, and more recently the three-hybrid system, have been found to be particularly effective methods.

The two-hybrid system is based on the reconstitution of a transcription activator in yeast (Fields S. and Song O., 1989; Chien C.-T. et al., 1991). A first protein is cloned by fusion with the DNA binding domain, while a second protein is cloned by fusion with the transcription activation domain. When the two proteins of interest interact together, a transcription activator is formed which allows the transcription of reporter genes.

Again using the two-hybrid principle, by inserting a DNA sequence encoding a third partner into the vectors used, a three-hybrid system has been developed by Zhang and Lautar (Zhang J. et al., 1996).

However, the two-hybrid and three-hybrid systems currently available have the major drawback that it is necessary to carry out a test of interaction with a negative control, which corresponds to performing the following two separate experiments:

a first experiment in which the host cells are transformed with vectors containing the DNA sequence encoding the test protein, and the DNA sequences encoding the potential partner(s) of this test protein, and a second experiment which serves as a negative control, in which the host cells are transformed with vectors not containing the DNA sequence encoding the test protein, but only those encoding the potential partner(s) of this test protein.

These two experiments are distinct since the host cells are transformed with different vectors depending on the experiment carried out.

Besides the fact that this need to carry out these two separate experiments does not allow rapid monitoring of the influence of the test protein on the other partner(s), the absence of growth of these negative controls often results from possible mutations or recombinations in one of the vectors, thus leading to erroneous results.

One of the aims of the present invention is, specifically, to provide new methods for studying interactions between proteins which do not need two separate experiments to be carried out and are consequently simpler and faster to perform and more reliable than the methods currently provided.

The invention relates to the use of at least one conditional promoter for carrying out a method for detecting one (or more) protein(s) (or polypeptides) interacting directly or indirectly with at least two other proteins (or polypeptides) during the formation of a protein complex or during the inhibition of the formation of a protein complex.

The expression "protein interacting directly with at least two other proteins during the formation of a protein complex" means:

any protein which combines with at least two other proteins to form with the latter a protein complex consisting of at least three proteins, or any protein which catalyses the formation of a protein complex between at least two proteins (but without combining with these proteins to form a protein complex), in particular by means of a mechanism of conformational modification of one or more of the partners of the protein complex.

The expression "protein interacting directly with at least two other proteins during the inhibition of the formation of a protein complex" means:

any protein which inhibits the formation of the protein complex consisting of at least these two other above-mentioned proteins, in particular by means of a mechanism of competition with one of the partners of the protein complex, or any protein which catalyses the inhibition of the formation of the protein complex consisting of at least these two other proteins, in particular by means of a mechanism of conformational modification of one or more of the partners of the said protein complex.

Among the conditional promoters which can be used in the context of the present invention, mention may be made of:

the promoter Met25 (Kerjan P. et al., 1986), which can be regulated as a function of the methionine concentration, or the promoters GAL1 or GAL10 (Johnston and Davis, 1984), which can be regulated as a function of the galactose concentration.

The invention also relates to any method for detecting a protein as defined above which interacts with at least two given proteins, during the formation of a protein complex or during the inhibition of the formation of a protein complex, characterized in that it comprises:

a step of transforming host cells whose genome contains one or more reporter genes with one or more vectors such that the genome of these host cells contains the DNA sequence encoding the test protein capable of being detected as well as the DNA sequences encoding at least two given proteins, the transcription of at least one of the DNA sequences being placed under the control of a conditional promoter, a comparison of the effects of repression of the conditional promoter with the effects of activation of this conditional promoter on the possible transcription of the abovementioned reporter gene(s), it being possible to correlate the results of this comparison with the detection of an interaction or, on the contrary, the absence of an interaction between the test protein and the given proteins.

The method described above for detecting a protein interacting directly or indirectly with at least two given proteins preferably comprises:

a step of transforming host cells whose genome contains one or more reporter genes with one or more vectors such that the genome of these host cells contains:

on the one hand the DNA sequence encoding the said test protein capable of interacting with at least two given proteins, the transcription of this DNA sequence being placed under the control of a conditional promoter, and on the other hand the DNA sequences encoding the said given proteins, a comparison of the effects of repression of the conditional promoter with the effects of activation of this conditional promoter on the possible transcription of the abovementioned reporter gene(s), it being possible to correlate the results of this comparison with the detection of an interaction or, on the contrary, the absence of interaction between the said test protein and the said given proteins.

In the text hereinabove and hereinbelow, the expression "transforming host cells with a vector" means any method for inserting the content of DNA sequences of a vector, in particular a vector of the plasmid type, into the genome of the said cells; the resulting host cells are denoted hereinabove and hereinbelow by the expression "transformed host cells". The expression "genome of a cell" means all the DNA contained in a cell, i.e. the chromosomal, mitochondrial and episomal DNA.

Thus, the method of the invention has the advantage of not comprising two separate experiments as described above, one of which serving as a negative control by parallel culturing of host cells transformed with vectors not containing any DNA sequence encoding the test protein, for the purpose of comparison with the step of culturing the host cells transformed with vectors containing all the DNA sequences encoding the proteins capable of interacting with each other.

The reason for this is that the host cells cultured in the method of the present invention, either as a negative control (or an internal control) or to demonstrate an interaction between the proteins, are transformed with the same vectors, thus avoiding the production of erroneous results, as indicated above in the context of the methods currently provided in this field.

Thus, one of the particularly advantageous aspects of the methods of the invention is that the control is intrinsic to the experiment, thereby making these methods particularly suitable for screening a cDNA library or a degenerate synthetic library of oligonucleotides which are liable to contain one (or more) DNA sequence(s) encoding one (or more) protein(s) interacting with at least two other given proteins.

The invention more particularly relates to any method as described above in which:
- of two of the proteins encoded by the DNA sequences contained in the vector(s) used for the transformation of the said host cells, one is fused with a DNA binding domain and the other is fused with a transcription activation domain, the transcription of the DNA sequences encoding these two fusion proteins being under the control of constitutive promoters,
- the other of these proteins, or at least one of the other proteins encoded by the DNA sequence(s) contained in the abovementioned vector(s), is encoded by a DNA sequence whose transcription is under the control of a conditional promoter.

Advantageously, of the two given proteins, or at least two of the said given proteins, encoded by the DNA sequences contained in the vector(s) used for the transformation of the said host cells, one is fused with a DNA binding domain, and the other is fused with a transcription activation domain, the transcription of the DNA sequences encoding these two fusion proteins being under the control of constitutive promoters.

Among the DNA binding domains which can be used in the context of the present invention, mention may be made of:
- LexA (described in particular in Vojtek A. et al., 1993), or
- GAL4 AD (described in particular in Fields S. and Song O., 1989, and Chien C.-T. et al., 1991, mentioned above),
- ERE (*Estrogen Response Element*) (described in particular in Klein-Hitpass L. et al., 1986, and in Le Douarin B. et al., 1995).

Among the transcription activation domains which can be used in the context of the present invention, mention may be made of:
- the VP16 transcription activator (described in particular in Vojtek A., mentioned above), or
- GAL4 AD (described in particular in Fields S. and Song O., 1989, and Chien C.-T. et al., 1991, mentioned above).

The abovementioned method of the invention can be carried out using a vector containing all of the DNA sequences encoding the proteins under consideration, or, preferably, using several vectors constructed such that:
- one of them contains the DNA sequence encoding the protein fused with the DNA binding domain and whose transcription is under the control of a constitutive promoter, while another vector contains the DNA sequence encoding the protein fused with the activation domain and whose transcription is also under the control of a constitutive promoter,
- one of the two abovementioned vectors, or another vector, contains a DNA sequence encoding a protein capable of interacting with the above proteins and whose transcription is under the control of a conditional promoter,
- where appropriate, one or more of the abovementioned vectors, or one or more other vectors, contain one or more DNA sequences encoding a protein capable of interacting with the above proteins and whose transcription is under the control of a conditional promoter (which is advantageously different from the above conditional promoter) or constitutive promoter.

The abovementioned method of the invention is advantageously carried out using several vectors such that:
- one of them contains a DNA sequence encoding one of the given proteins fused with the DNA binding domain and whose transcription is under the control of a constitutive promoter, while another vector contains a DNA sequence encoding another given protein fused with the activation domain and whose transcription is also under the control of a constitutive promoter,
- one of the two abovementioned vectors, or another vector, contains the DNA sequence encoding the test protein capable of interacting with the above proteins and whose transcription is under the control of a conditional promoter,
- where appropriate, one or more of the abovementioned vectors, or one more other vectors, contain one or more DNA sequences encoding another given protein capable of interacting with the above proteins and whose transcription is under the control of a conditional promoter which is different from the above conditional promoter or under the control of a constitutive promoter.

By way of illustration, the detection of an interaction between a test protein and two given proteins can be carried out using two vectors such that:
- one of them contains the DNA sequence encoding the protein fused with the DNA binding domain,
- the other vector contains the DNA sequence encoding the protein fused with the activation domain,
- one of the two abovementioned vectors contains the DNA sequence encoding the test protein capable of interacting with the above proteins and whose transcription is under the control of a conditional promoter.

The abovementioned method according to the invention for detecting an interaction between a test protein and two given proteins can also be carried out using three vectors such that:

the first vector contains the DNA sequence encoding the
protein fused with the DNA binding domain, the second vector contains the DNA sequence encoding
the protein fused with the activation domain, the third vector contains the DNA sequence encoding the
test protein capable of interacting with the above proteins and whose transcription is under the control of a
conditional promoter.

The abovementioned vectors also advantageously contain
a DNA sequence corresponding to a selection gene, such as
a gene encoding an enzyme for the metabolism of a specific
amino acid for which the transformed host cell strain is
auxotrophic.

The host cells transformed with the abovementioned
vectors, in the context of the implementation of a method
according to the invention, are advantageously such that
their genome comprises one or more reporter genes each of
whose transcription is placed under the control of an operator recognized by the DNA binding domain encoded by one
of the abovementioned vectors, the transcription of these
reporter genes taking place when there is formation, where
appropriate under the direct or indirect influence of the test
protein, of a protein complex between the given proteins
produced in the transformed host cells cultured.

Among the reporter genes which may be contained in the
genome of the host cells, mention may be made, for
example, of:

any gene encoding an enzyme capable of reacting with a
given substrate under conditions which make it possible to detect, or even to measure, the result of this
enzymatic reaction in the medium in which the transformed cells are cultured, in particular an enzyme
which reacts with a substrate in a colour reaction, for
example the LacZ gene which makes it possible to
detect, or even to measure, a β-galactosidase activity;
such a β-galactosidase activity can be reflected, for
example, by a blue coloration using 5-bromo-4-chloro-3-indolyl-β-D-galactoside (or Xgal) as substrate, or
alternatively by a yellow coloration using
O-nitrophenyl-β-galactoside (ONPG) as substrate, any gene encoding an enzyme responsible for the metabolism of a specific compound, in particular an amino
acid, for which the transformed host cell strain is
auxotrophic.

The host cells used are advantageously auxotrophic for
the amino acids whose metabolism is dependent on enzymes
encoded by the selection genes contained in the abovementioned vectors and, where appropriate, for the amino acid
whose metabolism is dependent on the enzyme encoded by
a reporter gene contained in the genome of the said host
cells.

By way of example, the host cell strain used is a yeast
strain, in particular the L40 yeast strain, the genome of
which contains, in terms of reporter genes, the HIS3 gene
(encoding an enzyme for the metabolism of histidine) and
the LacZ gene encoding β-galactosidase, the transcription of
these reporter genes being under the control of an operator
recognized by the LexA DNA binding domain.

In the detection of a protein as defined above which is
capable of interacting directly or indirectly with at least two
given proteins during the formation of a protein complex,
the DNA sequences encoding the said given proteins are
advantageously chosen from those encoding proteins which
form few or no protein complexes with each other.

In this case, there is no transcription, or least little
transcription, of the reporter gene(s) of the host cells transformed with the vector(s) defined above when these cells are
cultured while repressing the said conditional promoter
under whose control is placed the transcription of the DNA
sequence encoding the test protein or one of the given
proteins.

The transcription of the reporter(s) genes of the said host
cells cultured while activating the said conditional promoter,
or even an increased transcription of this or these reporter
genes compared with the transcription of these same genes
while repressing the said conditional promoter, can than be
correlated with the detection of a direct or indirect interaction between the test protein and the said given proteins
during the formation of a protein complex.

In the context of the detection of a protein as defined
above which is capable of interacting directly or indirectly
with at least two given proteins during the inhibition of the
formation of a protein complex, the DNA sequences encoding the said given proteins are advantageously chosen from
those encoding proteins which form a protein complex with
each other.

In this case, there is transcription of the reporter(s) of the
host cells transformed with the vector(s) defined above when
these cells are cultured while repressing the said conditional
promoter under whose control is placed the transcription of
the DNA sequence encoding the test protein.

The absence of transcription of the reporter gene(s) of the
said host cells cultured while activating the said conditional
promoter, or even the lesser transcription of this or these
genes compared with the transcription of these same genes
while repressing the said conditional promoter, can then be
correlated with the detection of a direct or indirect interaction between the test protein and the said given proteins
during the inhibition of the formation of a protein complex.

According to one particularly advantageous embodiment
of the methods of the invention which are described above:

the conditional promoter is the promoter Met25 which can
be regulated as a function of the concentration of
methionine in the culture medium of the transformed
host cells, the said promoter being activated in the
absence of methionine in the culture medium and
repressed in the presence of methionine, and the reporter genes contained in the genome of the transformed host cells are:

a gene encoding an enzyme for the metabolism of a
specific amino acid for which the strain of the said
host cells is auxotrophic by mutation in the said
gene, a gene coding encoding an enzyme responsible for the
coloration of the culture medium when it reacts with
its substrate, such as the LacZ gene encoding
β-galactosidase.

Thus, the detection, or even the measurement, of the
growth of colonies of the strain of transformed host cells in
a selective culture medium Ml which, on the one hand, does
not contain the amino acid whose metabolism is dependent
on the enzyme encoded by the reporter gene contained in the
genome of the said host cells and, on the other hand, does not
contain methionine can be correlated with the detection of
an interaction between the test protein and the given proteins
during the formation of a protein complex, since the growth
of these colonies in a selective culture medium M2 corresponding to the above culture medium Ml to which methionine is added is zero or less than that measured in the absence
of methionine.

Similarly, the detection, or even the measurement, of a
coloration in the culture medium of transformed host cells,
in particular a blue coloration in a medium containing the
substrate XGal, but not containing methionine, can be correlated with the detection of an interaction between the test protein and the given proteins during the formation of a protein complex, since this coloration in the above culture medium to which methionine is added is zero or less than that measured in the absence of methionine.

On the other hand, the absence of growth of colonies of the strain of transformed host cells in the abovementioned culture medium M1, or the detection of smaller growth of these colonies in the medium M1 compared with the growth detected for these colonies in the abovementioned medium M2, can be correlated with the detection of an interaction between the test protein and the given proteins during the inhibition of the formation of a protein complex.

Similarly, the absence of a coloration in the culture medium of the transformed host cells containing the specific substrate for the coloration (in particular XGal) but not containing methionine, or the detection of weaker coloration in this culture medium than in the culture medium containing methionine, can be correlated with the detection of an interaction between the test protein and the given proteins during the inhibition of the formation of a protein complex.

The present invention more particularly relates to the application of the methods described above to the screening of a cDNA library or a degenerate synthetic library of oligonucleotides which are liable to contain one (or more) DNA sequence(s) encoding one (or more) protein(s) as described above interacting directly or indirectly with at least two given proteins during the formation of a protein complex or during the inhibition of a protein complex.

By way of illustration, the detection of a protein interacting directly or indirectly with two given proteins A and B during the formation of a protein complex or during the inhibition of the formation of a protein complex is advantageously carried out according to the following method, which comprises:

the transformation of host cells with:
  a vector containing:
    a fusion DNA sequence between a DNA sequence encoding a given protein A and a DNA sequence encoding a DNA transcription activation domain, and
    a selection gene encoding an enzyme for the metabolism of an amino acid denoted hereinbelow as AA1,
  and a vector containing:
    a fusion DNA sequence between a DNA sequence encoding a given protein B which is different from the above protein A and a DNA sequence encoding a DNA binding domain, and
    a selection gene encoding an enzyme responsible for the metabolism of an amino acid denoted hereinbelow as AA2, AA2 being different from AA1,
one of the two abovementioned vectors containing a DNA sequence encoding the test protein, the transcription of this DNA sequence being under the control of the conditional promoter Met25,
the said host cells being such that their genome comprises a reporter gene, in particular the LacZ gene, as well as a gene encoding an enzyme for the metabolism of an amino acid denoted hereinbelow as AA3, AA3 being different from AA1 and AA2, and such that they are auxotrophic for the amino acids AA1, AA2 and AA3,
the selection of host cells transformed with the two abovementioned vectors by culturing these cells in a selective medium (M0) comprising AA3, but not containing AA1 or AA2,
the culturing of the transformed host cells selected during the above step, by activating the said conditional promoter in a selective culture medium M1 not containing AA1, AA2 or AA3 and not containing methionine,
a step of culturing the transformed host cells in a selective culture medium M2 while repressing the said conditional promoter, where M2 corresponds to the medium M1 to which methionine is added, this culturing step being carried out before, after or in parallel with the above culturing step,
the possible detection of an interaction between the test protein and the given proteins in the manner indicated above.

According to one particularly advantageous embodiment of the methods of the invention, the DNA sequence encoding the test protein or one of the DNA sequences encoding a given protein is fused, in the abovementioned vector(s), with a DNA sequence encoding a peptide which can be recognised specifically by an antibody, in particular a DNA sequence encoding tag Haemagglutinin (tag HA), which can be recognized by the anti-HA antibody (described in particular in Hanke et al., 1992).

Thus, the formation of a protein complex during the implementation of the method according to the invention can also be checked by immunoprecipitation of the said complex using a total extract of the host cells cultured and an antibody as described above. This immunoprecipitation makes it possible to separate and purify the protein complex from the culture medium of the said cells and, where appropriate, to check the structure and/or biological activity of this complex, in particular to deduce therefor the nature of the interaction between the test protein and the given proteins during the formation of this complex (i.e.: direct or indirect interaction as described above).

Needless to say, the present invention is not limited to studying the mutual interaction between three proteins, and the method described above in the context of the study of interactions between three proteins can be adapted to the study of the interaction between four or five (or even more) proteins.

In this case, each DNA sequence encoding an additional test protein is introduced into one of the two vectors used in the method described above, or even into other additional vectors, and is advantageously under the control of a conditional promoter which is preferably different from the other conditional promoter(s) already used for monitoring the transcription of DNA sequences encoding other proteins in the abovementioned vectors.

The invention will be further illustrated with the aid of the following examples of the study of interactions between several proteins.

I- Study of the Interaction Between the Three Proteins Cdk7, Cyclin H and MAT1.

These three proteins are proteins of the multiprotein complex TFIIH which is essential for DNA transcription and repair (Svejstrup et al., 1996). This complex can be resolved into two sub-complexes: the "core" comprising 6 sub-units and the kinase complex formed of the three proteins, Cdk7, Cyclin H and MAT1. This latter complex also exists in free form in vivo. Previous two-hybrid and immunoprecipitation experiments using extracts of cells co-infected with viruses which have incorporated the corresponding cDNA showed that the proteins Cdk7 and Cyclin H interact with each other. It was not possible with the two-hybrid system to detect complexes of Cdk7/MAT1 or Cyclin H/MAT1 type.

A) Materials and Methods

The yeast strain L40, which is auxotrophic for histidine, leucine, tryptophan and adenine, and the plasmids pLex9-

3H, derived from the vector pBTM116 (Vojtek et al., 1993), and pVP16 were used.

Figure 1:
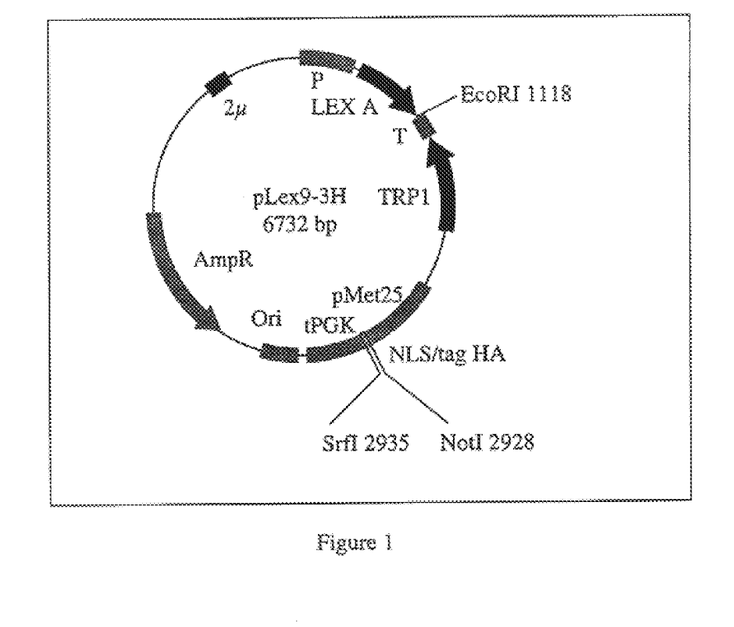

In addition to the selection marker TRP1 (gene encoding an enzyme for tryptophan metabolism) and LexA (containing a DNA binding domain) cloned downstream of the alcohol dehydrogenase (ADH) constitutive promoter, pLex9-3H comprises an expression cassette consisting of the inducible promoter Met25, a tag Haemagglutinin (tag HA), a nuclear localization signal (NLS), the cloning sites NotI and SrfI for incorporating the DNA encoding a polypeptide of interest, and the phosphoglycerate kinase transcription terminator, tPGK (FIG. 1).

The plasmid pVP16 contains a selection marker LEU2 (gene coding encoding an enzyme for leucine metabolism) and the VP16 transcription activator cloned downstream of the ADH promoter.

Figure 2:
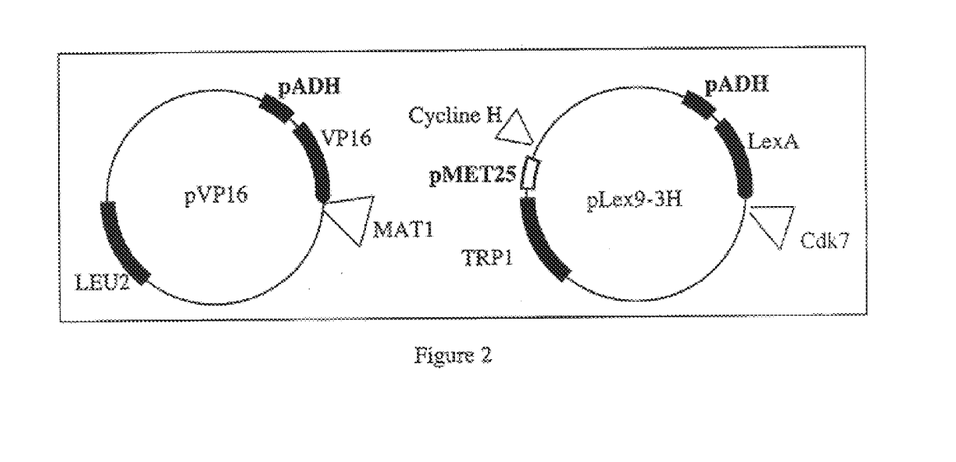

The cDNAs encoding Cdk7, Cyclin H and MAT1 were respectively cloned by fusion with LexA into the plasmid pLex9-3H, under the dependence of the promoter Met25 in pLex9-3H, and by fusion with VP16 into the plasmid pVP16 (FIG. 2).

a) Construction of the Plasmids

The cDNAs encoding each of the three proteins were amplified by PCR using constructs described in Adamczewski J. P. et al., 1996, with nucleotides specific to each of them, after which they were inserted into the appropriate vectors.

PCR allowing the cloning of Cdk7 by fusion with LexA into the EcoRI site of pLex9-3H was carried out with the oligonucleotides 5' AGTCGTGAATTCATGGCTCTG-GACCTGAAG3' (SEQ. ID NO: 1) for the 5' portion of the cDNA and 5' GATCGTGAATTCTTAAAAAATT-AGTTTCTTGGGCAA3' (SEQ. ID NO: 2) for the 3' end, the resulting fusion protein being LexA-Cdk7. PCR allowing the cloning of Cyclin H by fusion with tag HA into the NotI site of pLex9-3H downstream of the promoter pMet25 was carried out with the oligonucleotides 5' GATCGTGCGGC-CGCAATGTACCACAACAGT3' (SEQ. ID NO: 3) for the 5' portion of the cDNA and 5' GATCGTGCGGCCGCTTA-GAGAGATTCTACCAG3' (SEQ. ID NO: 4) for the 3' end, the resulting fusion protein being TagHA-Cyclin H. Finally, PCR allowing the cloning of MAT1 by fusion with VP16 into the EcoRI site of pVP16 was carried out with the oligonucleotides 5' GATCAGGAATTCCCATGGAGGAT-CAGGGTT3' (SEQ. ID NO: 5) for the 5' portion of the cDNA and 5' GATCAGGAATTCTTAACTGGGCTGCCA-GAA3' (SEQ. ID NO: 6) for the 3' end, the resulting fusion protein being VP16-MAT1.

b) Transformation of the Yeast and Selection of the Transformants

The strain L40 [MATa, trp1, his3, leu2, ade2, LYS2:: (LexAop)$_4$-HIS3, URA3:: (LexAop)$_8$-LacZ] contains the reporter genes HIS3 (encoding an enzyme for histidine metabolism) and LacZ fused with an operator recognized by LexA. The cells are cultured for 16 hours in complete medium (YPD medium) and transformed with Cdk7-pLex9-3H-CyclinH by the lithium acetate method (Schiestl R. H. et al., 1993). Since pLex9-3H contains the TRP1 gene, the selection of the transformants is carried out on HLA minimum medium (containing 0.06 g/l of histidine, 0.12 g/l of leucine and 0.12 g/l of adenine, in addition to the 1.44 g/l of "yeast nitrogen base without amino acids" and the 20 g/l of agarose, but without tryptophan). One of the transformed clones is then recultured in 20 ml of HLA overnight, and then transformed in its turn with MAT1pVP16 in the same way as before. Since pVP16 comprises the LEU2 gene, selection of the double transformants will be carried out on HA minimum medium (containing adenine and histidine, but no tryptophan or leucine).

c) Expression of the Proteins

The expresssion of the proteins is monitored by immunoblots carried out using extracts of yeasts which have grown on HA medium, which is a medium that is selective for the presence of plasmids. The repression induced by the presence of methionine is also examined (Rose M. D., 1990).

d) Test of Interaction Between the Three Partners

Two types of monitoring are available: the growth test and the test of β-galactosidase activity.

For the growth test, three different clones, isolated from cultures established on HA medium, are suspended in 50 μl of sterile water and diluted in cascade from 10 down to $10^{-4}$. For each of the clones, one drop of each dilution is deposited on medium selective for the triple interaction (A, containing only adenine) as well as on a medium which inhibits the expression of Cyclin H (AM, containing 1 mM methionine and adenine).

The β-galactosidase activity is evaluated on cells which have been grown overnight in adequate medium (the optical density at 600 nm [$OD_{600}$] will be measured) and then resuspended in a phosphate buffer (according to Miller J., 1972) to which are added three drops of chloroform and two drops of 0.1% SDS detergent for incubation for 5 minutes at 28° C.; the reactivation is initiated with 200 μl of O-nitrophenyl-β-galactoside (ONPG) at 4 mg/ml and then stopped with 500 μl of 1 mM bicarbonate $Na_2CO_3$ as soon as a pale yellow colour appears. The $OD_{420}$ is then measured. The β-galactosidase activity (in $ml^{-1}.min^{-1}$) is calculated by the formula: $(OD_{420})/[(OD_{600}) \times vol.$ of culture (ml)×reaction time (min))]. (Rose M. D., 1990).

B) Results

Figure 3A:
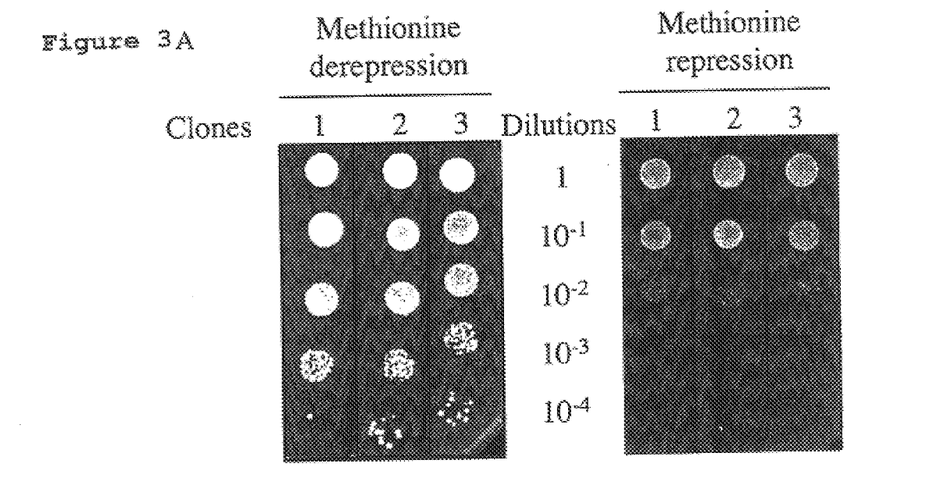
Figure 3B:
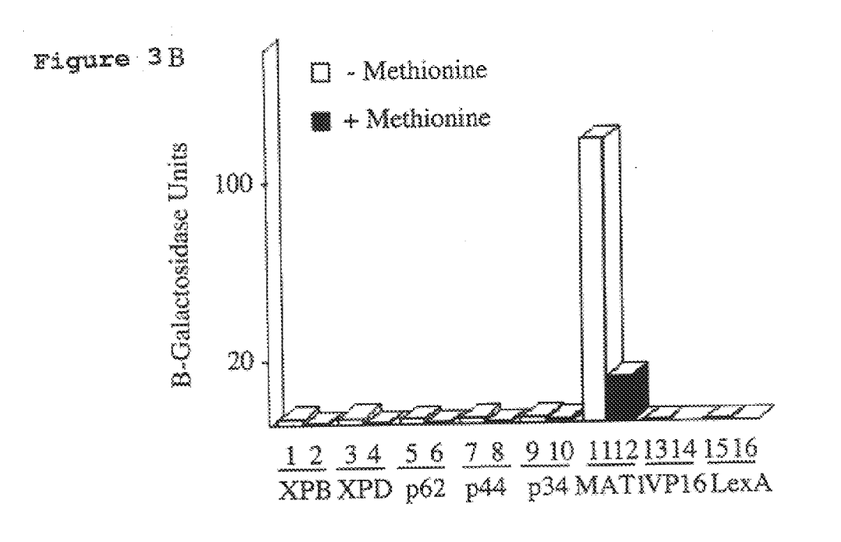
Figure 4:
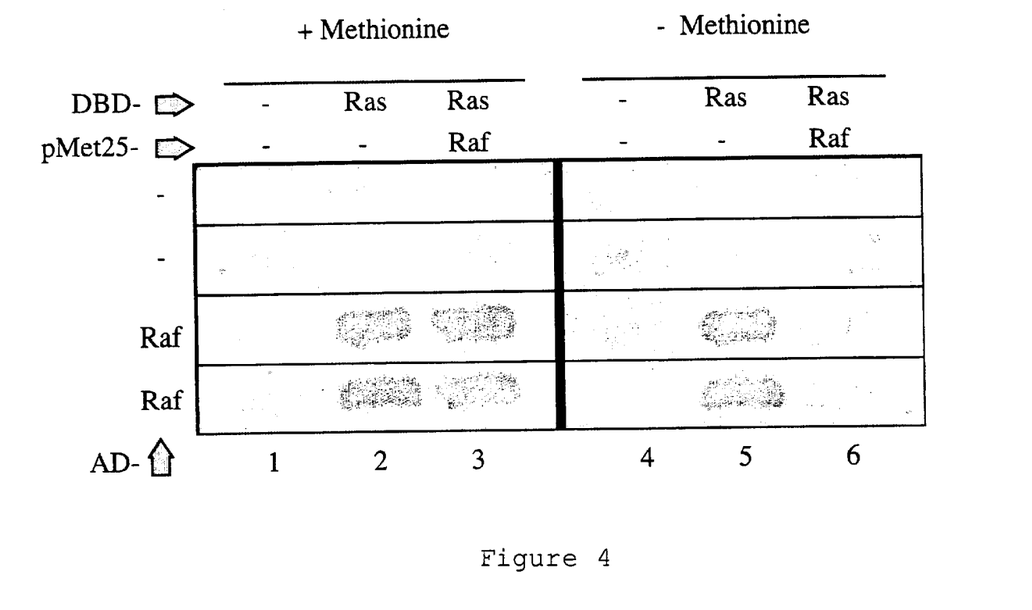

In a methionine-free medium (allowing the expression not only of Cdk7 and MAT1, but also of Cyclin H), the growth of colonies is observed for dilutions ranging from $10^{-1}$ to $10^{-4}$, while on a methionine-rich medium (repression of Cyclin H), colonies are observed only for the first two dilutions (FIG. 3). Furthermore, the measurement of the β-galactosidase activity of the strain which has been grown on the methionine-free medium is 115 $ml^{-1}.min^{-1}$, while that of the same strain which has been grown in the presence of methionine shows an activity of 18 $ml^{-1}.min^{-1}$, i.e. a more than 6-fold inhibition of the β-Gal activity (FIG. 4).

These results demonstrate that the third polypeptide Cyclin H catalyses (stabilizes) the formation of the activation pair Lex-Cdk7/VP16-MAT1, which might be due to the formation of a triple complex between Cdk7, Cyclin H and MAT1.

The low β-galactosidase activity visualized when Cyclin H is repressed suggests a weak association between MAT1 and Cdk7; this cannot be excluded on the basis of the immunoprecipitation experiments carried out on insect cell extracts, in which a weak Cdk7/MAT1 association was visualized.

In order to check the specificity of the interaction: Cdk7/Cyclin H/MAT1, we incorporated the other sub-unit of the TFIIH complex into the vector pVP16. Thus, five sub-units of the TFIIH core were tested for an association with Cdk7 in the presence of Cyclin H. No interaction could be visualized, either by growth test or by the β-galactosidase test as illustrated (FIG. 4). The expression of Cdk7 and Cyclin H (Cdk7-pLex9-3H-Cyclin H), on the one hand, and of VP16 alone (not containing any fused protein), on the other hand, gives a response equivalent to the background noise, both for the growth test and for the test of β-galactosidase activity (FIG. 4).

The results of the interaction tests on the one hand and the presence of the three proteins demonstrated by Western blotting on the other hand strongly suggest the existence of a ternary complex containing the proteins Cdk7, Cyclin H and MAT1. In order to visualize such a ternary complex, a total extract of yeast which has been grown on medium A was immunoprecipitated by means of the fusion peptide tag HA of Cyclin H. Thus, the anti-HA antibody retains not only Cyclin H, but also Cdk7 and MAT1. Furthermore, the complex thus purified has the same type of CTD kinase activity as the complex isolated by other means.

II. Inhibition of the Interaction Between the Proteins Ras and Raf

Ras and Raf are two oncogene proteins which interact together with, as a consequence, a potential involvement in the translation of the signals which control the phenomena of cell growth and differentiation.

The inhibition of contact of these two proteins can be studied either by screening an oligopeptide library or by involving a third partner which is identical to one of the other two polypeptides forming the transcription activator, but containing no fusion sequence. In order to monitor the specificity of the Ras/Raf interaction, the third partner will be under the control of the inducible promoter Met25.

A) Materials and Methods

A cassette containing the promoter Met25, an HA epitope and a DNA fragment encoding a nuclear localization sequence, a NotI site, either a BglII site or an SrfI site, a Stop codon and the PGK terminator was inserted into the single PvuII site of the plasmids pGBT9 (Bartel et al., 1993), pGBT10 (Chardin et al., 1993), pHP5, pBTM116 (Vojtek et al., 1993) and pVJL10 (Julien-Flores et al., 1995), giving the plasmids pGBT9-3H, pGBT10-3H, pGBT11-3H, pLex9-3H, and pLex10-3H, respectively. Expression of the promoter Met25 is repressed in the presence of 1 mM methionine.

The plasmids derived from pGBT9-3H were constructed in the following way: the reading frame (ORF) of H-Ras (V12) (EcoRI-SalI fragment of pBTM116-Ras (Vojtek et al., 1993)) was cloned in phase with the DNA binding domain of GAL4, the resulting plasmid being [pGBT-Ras/Met-0]. The plasmid [pGBT-Ras/Met-Raf] was obtained by adding, on either of the EcoRI-BamHI fragment of cRaf-1 originating from the plasmid pGAD-Raf (Van Aelst et al., 1993), a binding sequence containing the NotI cloning site, and then by cloning the resulting fragment into the NotI site of the Met25 expression cassette of [pGBT-Ras/Met-0].

B) Results

The cells co-transformed with [pGBT-Ras/Met-Raf] and pGAD-Raf are LacZ+ (transcription of the β-galactosidase gene) in the presence of methionine, i.e. under conditions of repression of the promoter Met25. The same cells are LacZ- in the absence of methionine, i.e. under conditions of derepression of the promoter Met25. This observation can be explained by the fact that wild-type Raf protein expressed using the promoter Met25 enters into competition for interaction with the protein expressed using [pGBT9-Ras/Met-Raf], thus inhibiting the interaction between the fusion proteins GAD4DBD-Ras and GAL4AD-Raf.

Previous controls showed that the presence of the inducible promoter Met25 does not affect the interaction between the two products arising from the fusion sequences, whether this promoter is active or repressed.

The plasmids described above can be used to identify peptides which inhibit an interaction between proteins, for example by expressing a degenerate synthetic library of oligonucleotides under the control of the promoter Met25.

The inhibition of the interaction can be detected by means of a LacZ test under conditions of derepression of the promoter Met25; the phenotype LacZ+ may be restored in the presence of methionine, proving that the inhibition is due to expression of the promoter Met25 but not due to other events such as a mutation.

TABLE 1

| Name | ADH sub-promoter, fused with GAL-DBD | Met25 sub-promoter, fused with HA-NLS |
| --- | --- | --- |
| pGBT935 | — | — |
| pGBT935-Ras, Met25-0 | c-H-Ras | — |
| pGBT935-Ras, Met25-Raf | c-H-Ras | c-Raf-1 |

Legend for Table 1:

In pGBT935, the insertion of the cDNA encoding the Ras protein (c-H-Ras; Vojtek, 1993) in phase with the region encoding the GAL4 DNA binding domain (GAL-DBD) leads to the plasmid [pGBT935, Met25-0]; the cDNA encoding the Raf protein (c-Raf-1; Van Aelst, 1993) cloned in phase with the region encoding the nuclear localization site linked to the HA epitope (HA-NLS) into the plasmid [pGBT935, Met25-0] leads to the plasmid [pGBT935, Met25-Raf]. The plasmid pGAD-Raf allows the expression of a protein c-Raf-1 fused with the GAL4 activation domain (AD-Raf).

BRIEF DESCRIPTION OF THE DRAWINGS

FIG. 1:

The vector pLex9-3H derived from the vector pBTM116. The portion pBTM116 contains, in addition to the sequences required for its replication in *E. coli*, the TRP1 selection marker and the LexA transcription activator cloned downstream of the promoter (P) and upstream of the terminator (T) of ADH. pLex9-3H also has an expression cassette containing the regulatable promoter Met25, a tag HA, a nuclear localization sequence (NLS) and a terminator tPGK. The cDNA insertion sites of interest are indicated.

FIG. 2:

The cDNA encoding Cdk7 is cloned by fusion with LexA, that of cyclin H is fused with tag HA, downstream of the regulable promoter Met25, into the plasmid pLex9-3H, while the cDNA and MAT1 is cloned by fusion with VP16 into the plasmid pVP16. This plasmid contains the selection marker LEU2 and the VP16 activation domain downstream of the ADH constitutive promoter.

FIG. 3(panel A & B):

A: test of growth of three clones of yeasts transformed with the plasmids Cdk7-pLex9-3H-cyclin H and MAT1-pVP16 on a methionine-free medium (Met-: methionine derepression) and a methionine-rich medium (Met+1 mM: methionine repression). The different dilutions are indicated in the centre of the figure.

B: β-galactosidase activity of extracts of yeasts transformed with the vectors Cdk7-pLex9-3H-cyclin H, on the one hand, and the vectors expressing the protein VP16 fused with XPB, XPD, p62, p44, p34 or MAT1 or VP16 alone (VP16), on the other hand, which have been grown in the presence (+) or absence (−) of methionine. The β-gal units are indicated in ml$^{-1}$.min.$^{-1}$.

FIG. 4:

The HF7c yeast strain cells co-transformed with plasmid pairs are selected in a medium not containing tryptophan or leucine (Rose, 1990); the colonies are distributed in a medium containing no tryptophan or leucine, and containing or not containing methionine. After 24 hours at 30° C., the dishes were re-inoculated to test the hypotrophy to histidine (results not shown) and for the expression of LacZ (Chardin, 1993), in the presence or absence of methionine.

References

Adamczewski J. P., Rossignol M., Tasan J. P., Nigg E. A., Moncollin V. and Egly J. M. (1996), *EMBO J.*, 15, 1877–1884.

Bartel P. L., Chien C.-T., Sternglanz R. and Fields S. (1993), in *Cellular Interactions in Development: A Practical Approach*. (Hartley D. A., ed.), 153–179, Oxford University Press, Oxford.

Chardin P., Camonis J. H., Gale N. W., Van Aelst L., Schlessinger J., Wigler M. H. and Bar-Sagi D. (1993), *Science* 260, 1338–1343.

Chien C.-T., Bartel P., Sternglanz R. and Fields S. (1991), *Proc. Natl Acad. Sci.*, 88, 9578–9582.

Fields S. and Song O. (1989), *Nature* (London), 340, 245–246.

Hanke et al. (1992), *J. Gen. Virol.*, 73, 653–660.

Johnston M. and Davis R. W. (1984). Sequences that regulate the divergent GAL1-GAL10 promoter in *Saccharomyces cerevisiae*. Molecular and Cellular Biology, 4, 1440–1448.

Julien-Flores V., Dorseuil O., Romero F., Letourner F., Saragosti S., Berger R., Tavitian A., Gacon G. and Camonis J. H. (1995), *J. Biol. Chem.*, 270, 22473–7.

Kerjan P., Cherest H. and Surdin-Kerjan Y. (1986). Nucleotide sequence of the Saccharomyces cerevisiae Met25 gene. *Nucleic Acids Research*, 14, 7861–7871.

Klein-Hitpass L. et al. (1986), *Cell*, 46, 1053–1061.

Le Douarin B. et al. (1995), *Nucleic Acids Research*, 23, 876–878.

Miller J. (1972), *Experiments in Molecular Genetics*, Cold Spring Harbor, NY; Cold Spring Harbor Laboratory Press.

Rose M. D., Winston F. Hieter P. (1990), *Methods in yeast genetics* A laboratory course manual Cold Spring Harbor, NY; Cold Spring Harbor Laboratory Press.

Schiestl R. H., Manivasakam P., Woods R. A. and Gietz R, D. (1993), *Methods*, 5, 79–85.

Svejstrup J. Q., Vichi P. and Egly J. M. (1996). The multiple roles of transcription/repair factor TFIIH. *Trend. Biol. Sci.*, 21, 346–350.

Van Aelst L., Barr M., Marcus S., Polverino A. and Wigler M. (1993), *Proc. Natl Acad. Sci.*, 90, 6213–6217.

Vojtek A., Hollenberg S. M. and Cooper J. A. (1993), *Cell*, 74, 205–214.

Zhang J. and Lautar S. (1996). A yeast three-hybrid method to clone ternary protein complex components. Analytical Biochemistry, 242, 68–72.

What is claimed is:

1. A method for detecting an interaction or an absence of interaction between a first protein and at least two other proteins, said interaction being (i) formation of a protein complex including said first protein and said at least two other proteins, or (ii) formation of a protein complex including said at least two other proteins, said formation being catalyzed by said first protein, or (iii) inhibition of formation of a protein complex among said at least two other proteins wherein the inhibition of protein complex formation is mediated by said first protein; said method comprising:

(a) transforming host cells with:
   i) a DNA sequence encoding said first protein, wherein transcription of said DNA sequence is controlled by a conditional promoter, and
   ii) DNA sequences encoding said at least two other proteins, wherein the genome of said host cells contains at least one reporter gene that is transcribed in the presence of a protein complex comprising the at least two other proteins, (b) comparing effects of repression of said conditional promoter with effects of activation of said conditional promoter on transcription of said at least one reporter gene, and (c) correlating the results of step (b) with detecting an interaction or the absence of interaction between said first protein and said at least two other proteins.

2. The method according to claim 1, wherein one of said at least two other proteins is fused with a DNA binding domain and another of said at least two other proteins is fused with a transcription activation domain, transcription of the DNA sequences encoding these two fusion proteins being under the control of constitutive promoters.

3. The method according to claim 1, wherein step (a) comprises introducing DNA sequences in the form of:

a first vector containing a DNA sequence encoding one of said at least two other proteins fused with a DNA binding domain and whose transcription is under the control of a constitutive promoter, and a second vector containing a DNA sequence encoding another of said at least two other proteins fused with an activation domain and whose transcription is also under the control of constitutive promoter, or a first vector containing a DNA sequence encoding one of said at least two other proteins fused with a DNA binding domain and whose transcription is under the control of a constitutive promoter, a second vector containing a DNA sequence encoding another of said at least two other proteins fused with an activation domain and whose transcription is also under control of a constitutive promoter and a third vector comprising the DNA sequence encoding said first protein, or a first vector containing a DNA sequence encoding one of said at least two other proteins fused with a DNA binding domain and whose transcription is under the control of a constitutive promoter, a second vector containing a DNA sequence encoding another of said at least two other proteins fused with an activation domain and whose transcription is also under control of a constitutive promoter and a third vector comprising at least one DNA sequence encoding a further one of said at least two other proteins whose transcription is either under the control of a second conditional promoter which different from the conditional promoter controlling expression of the first protein or is under the control of a constitutive promoter.

4. The method according to claim 1, wherein each said at least one reporter gene is transcribed under control of an operator recognized by a DNA binding domain of one of said said at least two other proteins.

5. The method according to claim 1, wherein:

the conditional promoter is the promoter Met25 which can be regulated as a function of the concentration of methionine in the culture medium of the transformed host cells, said Met25 promoter being activated in the absence of methionine in the culture medium and repressed in the presence of methionine, and the at least one reporter gene contained in the genome of the transformed host cells is selected from the group consisting of:

a gene encoding an enzyme capable of reacting with a given substrate under conditions which make it possible to detect the result of this enzymatic reaction in the medium in which the transformed cells are cultured; and a gene encoding an enzyme responsible for the metabolism of a specific compound, for which the transformed host cell strain is auxotrophic.

6. The method according to claim 1, wherein the first protein is a protein which catalyzes formation of a the protein complex between at least two of said other proteins, by a mechanism of conformational modification of at least one component of said protein complex.

7. The method according to claim 6 wherein:

the DNA sequences encoding said at least two other proteins are chosen from those encoding proteins which do not form a protein complex in the absence of said first protein, and wherein step (b) comprises correlating transcription of said at least one reporter gene with detection of an interaction between the first protein and said at least two other proteins during formation of a protein complex.

8. A method according to claim 1, wherein said first protein is selected from the group consisting of:

a protein which inhibits formation of a protein complex by said at least two other proteins, by a mechanism of competitions with a component of the protein complex, and a protein which catalyzes the inhibition of the formation of a protein complex with said at least two other proteins, by a mechanism of conformational modification of one or more components of the protein complex.

* * * * *